United States Patent [19]

de Witt

[11] 4,401,827

[45] Aug. 30, 1983

[54] NOVEL ACYL-DERIVATIVES OF CARNITINE AND PROCESS FOR THEIR PREPARATION

[75] Inventor: Paolo de Witt, Rome, Italy

[73] Assignee: Sigma-Tau, Rome, Italy

[21] Appl. No.: 334,604

[22] Filed: Dec. 28, 1981

Related U.S. Application Data

[63] Continuation of Ser. No. 52,283, Jun. 26, 1979, abandoned.

[30] Foreign Application Priority Data

Jun. 27, 1978 [IT] Italy .............................. 50065 A/78

[51] Int. Cl.$^3$ ............................................ C07C 69/74
[52] U.S. Cl. ......................................... 560/1; 560/55; 560/56; 560/59; 560/104; 560/147; 560/153; 560/155; 560/170; 560/171; 560/174; 560/176; 560/180; 560/196; 560/222; 560/226; 424/308; 424/309; 424/311; 424/313; 424/314

[58] Field of Search ................. 560/1, 65, 56, 59, 104, 560/147, 153, 155, 170, 171, 174, 176, 180, 196, 222, 226

[56] References Cited

U.S. PATENT DOCUMENTS 4,194,006 3/1980 Cauazza .............................. 424/311

OTHER PUBLICATIONS

Chemical Abstract 64 19398-99.
Chemical Abstract 52 3066g.
Chemical Abstract 54 14447e.

Primary Examiner—Paul J. Killos
Attorney, Agent, or Firm—Ladas & Parry

[57] ABSTRACT

Novel acyl-derivatives of the $\beta$-hydroxy-$\gamma$-butyrobetaine are disclosed (typically pyruvyl carnitine hydrochloride) which are useful therapeutic agents in the treatment of cardiac disorders, hyperlipidoemias and hyperlipoproteinemias.

5 Claims, No Drawings

NOVEL ACYL-DERIVATIVES OF CARNITINE AND PROCESS FOR THEIR PREPARATION

This is a continuation of application Ser. No. 052,283, filed June 26, 1979, now abandoned.

The present invention relates to novel acyl derivatives of carnitine ($\beta$-hydroxy$\gamma$-butyrobetaine) and a process for their preparation.

More particularly, the present invention relates to acyl derivatives of carnitine having general formula:

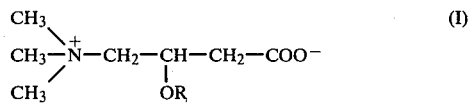

wherein R is the monovalent radical of the following organic acids: 3-bromo propionic, cyclohexylcarboxylic, cyclohexylpropionic, diethylacetic, dipropylacetic, dibutyrylacetic, 4-chlorobutyric, 2-ethylhexanoic, pivalic, cinnamic, p-methylcinnamic, p-chlorocinnamic, p-methoxycinnamic, phenylacetic, p-isobutylphenylacetic, p-methylphenylacetic, p-ethylphenylacetic, p-cyclohexylphenylacetic, p-cyclopropylphenylacetic, p-isobutyl m-chlorophenylacetic, $\alpha$-phenylpropionic, p-isobutyl $\alpha$-phenylpropionic, p-methyl $\alpha$-phenylpropionic, p-ethyl $\alpha$-phenylpropionic, p-cyclohexyl $\alpha$-phenylpropionic, p-cyclopropyl $\alpha$-phenylpropionic, p-isobutyl $\alpha$phenylpropionic, malonic (monoester), glutaric (monoester), adipic (monoester), pimelic (monoester), suberic (monoester), azelaic (monoester), sebacic (monoester), pyruvic, levulinic, $\alpha$-ketoglutaric (monoester), $\beta$-ketoglutaric (monoester), fumaric (monoester), citric (monoester), isocitric (monoester), oxalacetic, $\gamma$-acetylaminobutiric, $\epsilon$-acetylaminocaproic, N-acetylaspartic (monoester), N-acetylglutamic (monoester), N-acetyl-5 amidoglutamic (monoester), N-acetylcysteine, S,N-diacetylcysteine, N-acetyl leucine, N-acetyl isoleucine, N-acetylmethionine, N-acetylvaline, $\alpha$-methylglutaric (monoester), $\alpha$-methyl-$\alpha$-hydroxyglutaric (monoester), $\alpha$-methylene butyric, $\beta$-methylene butyric, m-trifluoromethylcinnamic, m-bromo-cinnamic and 2-naphtalene acetic.

The present invention relates to compounds of formula (I) in their optically active forms (i.e. D- and L-isomer) as well as in their racemic form (D, L), and also relates to their corresponding pharmaceutically acceptable salts, both in their optically active and racemic form.

The compounds of general formula (I) can be prepared either as such or as salts with mineral acids or aliphatic and aromatic, mono or pluricarboxylic acids or with sulfonic acids or with sulfamic acids.

Generally, the compounds of formula (I) and their pharmaceutically acceptable salts have shown interesting cardiotropic hyperlipoproteinemic and hyperlipidaemic properties.

The compounds of formula (I) are normally prepared as hydrochlorides. It is in fact preferred to react $\beta$-hydroxy $\gamma$-butyrobetaine hydrochloride with the acyl chlorides wherein the acyl radical R has the above-defined meaning.

The reaction for preparing these novel acyl-derivatives takes place normally at a temperature between 0° C. and 80° C. under anhydrous conditions and in the presence of an excess of trifluoroacetic acid. When the acyl chloride is solid and not easily soluble in trifluoroacetic acid, it is possible to improve its solubility, in such a way as to obtain a homogenous phase, by adding a small amount of a chlorine-containing solvent, such as anhydrous methylene chloride or chloroform.

Particular care for keeping the reaction zone under anhydrous conditions should be taken, by shielding the reaction zone with $CaCl_2$-containing tubes.

At the end of the reaction, the mixture thus obtained is cooled and usually treated with acetone; any solid which may separate is discharged, whereas the precipitate which forms upon addition of ethyl ether is collected.

The precipitated product can be purified by crystallization with further ethyl ether. Generally, one or two crystallizations are sufficient in order to obtain a product having a high degree of purity which can be checked by thin layer chromatography using silica plates and various eluents such as $CHCl_3$-MeOH-conc. $NH_4OH$ (50:30:8 v/v) or n-BuOH-acetic acid-$H_2O$ (60:20:20 v/v).

Generally, the reaction yields vary from 60 to 85%, disregarding any possible lowering which may occur upon purification by crystallization.

In order to prepare the acyl-derivatives of carnitine wherein the acyl group is that derived by an $\alpha$- or $\beta$-ketoacid, it is preferred to firstly perform the protection of the keto group by converting it into a ketal.

The ketoacid is thus firstly converted into a ketoester and thereafter into a ketal by reacting the ketoester with ethylene glycol. The ketal of the ester is hydrolyzed to the acid ketal and then converted into acid chloride ketal with thionyl chloride. This acid chloride ketal is used in the reaction with $\beta$-hydroxy $\gamma$-butyrobetaine (carnitine) in accordance with the previously mentioned procedures. The protective carbonyl group is hydrolyzed during the reaction, and the isolated raw material comprises the desired acyl carnitine.

The following examples, beside showing several chemico-physical data concerning the main products of the present invention, illustrate the process of the present invention, without limiting the scope thereof.

EXAMPLE 1

Dipropylacetylcarnitine hydrochloride

To a solution of carnitine hydrochloride (3.94 g; 0.02 moles) in trifluoro acetic acid (9 mls), the acyl chloride of dipropylacetic acid (3.25 g; 0.02 moles) is added. The mixture is kept under stirring at room temperature for 24 hours.

70 mls. of acetone are added and the mixture is kept under stirring at 5° C. for 2 hours. The precipitated carnitine is filtered. To the solution 70 mls of ethyl ether are also added and the mixture is kept under stirring at 5° C. for 30 minutes. The solid thus formed is filtered. The raw product is crystallized from isopropanol-ethyl ether and 4.5 g (yield 70%) are obtained. M.P. 192° C.

NMR Spectrum ($D_2O$)$\delta$:

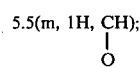

3.8 (d, 2H, N—$CH_2$);

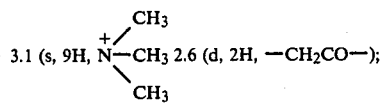

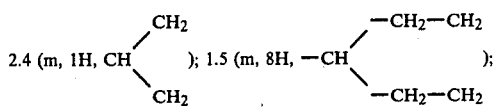

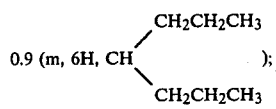

IR Spectrum (nujol) νco=1760 cm⁻¹ (C=O ester); νco=1700 cm⁻¹ (C=O acid).

Elementary analysis: C₁₅H₃₀NO₄Cl (M.W.=323.5)—Calculated: C, 55.63%; H, 9.33%; N, 4.32%; Cl, 10.97%. Found: C, 56.00%; H, 9.12%; N, 0.06%; Cl, 11.16%.

EXAMPLE 2

Pivaloyl carnitine hydrochloride 1.98 g (0.01 moles) of carnitine hydrochloride are dissolved in 3 mls of CF₃COOH, and to the solution an excess (7 mls) of pivalic acid chloride is added. The solution is kept under stirring at room temperature for about 48 hours. At the end of this period of time, the mixture is diluted with 20 mls of acetone and some ether is slowly added till complete precipitation. The mixture is filtered and the precipitate which has the tendency to become hygroscopic is quickly washed with ether and dried under vacuum at the temperature of about 50° C. 1.70 g are obtained with a yield of 60% of a product having the following characteristics:

M.P. 130°-35° C.

IR Spectrum (nujol) νco=1718 cm⁻¹ (C=O acid); νco=1740 cm⁻¹ (C=O ester).

NMR Spectrum (D₂O)δ:

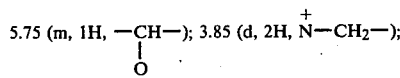

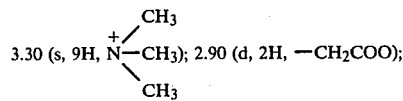

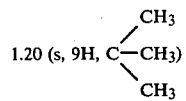

Elementary analysis: C₁₂H₂₄O₄NCl (M.W. 281.83)—Calculated: C, 51.13%; H, 8.60%; N, 4.97%; Cl, 12.58%. Found: C, 50.83%; H, 8.90%; N, 3.77%; Cl, 12.88%.

EXAMPLE 3

Cinnamoyl carnitine hydrochloride 4.55 g (0.023 moles) of carnitine hydrochloride are dissolved in 6.9 mls of CF₃COOH, and to the solution an excess (16 mls) of cinnamoyl chloride is added. The mixture is kept under stirring at 40°-45° C. for 4-5 hours. At the end of this period of time, the mixture is diluted with 60 mls of acetone and some ether is slowly added till complete precipitation. The mixture is filtered and the precipitate which has the tendency to become hygroscopic is quickly washed with ether and dried under vacuum at a temperature not exceeding 50° C.; 5.3 g of a product are obtained (yield 70%) having the following characteristics:

M.P. 207°-09° C.

IR Spectrum (nujol) νco=1710 cm⁻¹ (acid); νco=1740 cm⁻¹ (ester).

NMR Spectrum (D₂O)δ:

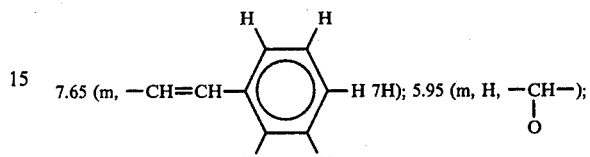

3.95 (d, 2H, N⁺—CH₂—);

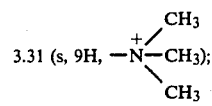

3.05 (d, 2H, —CH₂—CO—)

Elementary analysis: C₁₆H₂₂ClNO₄ (M.W. 327.85)—Calculated: C, 58.61%; H, 6.78%; N, 4.27%; Cl, 10.81%. Found: C, 58.01%; H, 6.38%; N, 4.07%; Cl, 10.51%.

EXAMPLE 4 p-methoxy cinnamoyl carnitine hydrochloride 7.12 g (0.036 moles) of carnitine hydrochloride are dissolved in 12 mls of CF₃COOH, and to the solution an excess (25 mls) of p-methoxy cinnamoyl chloride is added and the mixture kept under stirring at 40°-50° C. for 4-5 hours. At the end of this period of time the mixture is diluted with 90 mls of acetone and some ether is slowly added till complete precipitation. The mixture is filtered and the precipitate which has the tendency to become hygroscopic is quickly washed with ether and dried under vacuum at a temperature not exceeding 50° C; 9 g of a product are obtained (yield 70%) having the following characteristics:

M.P. 217°-20° C.

IR Spectrum (nujol) νco=1710 cm⁻¹ (acid); νco=1740 cm⁻¹ (ester).

NMR Spectrum (D₂O)δ:

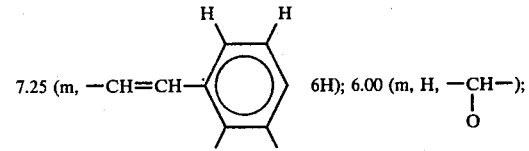

3.95 (d, NH, N⁺—CH₂—); 3.85 (s, 3H, O—CH₃);

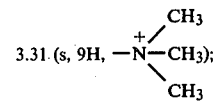

3.05 (d, 2H, —CH$_2$CO—)

Elementary analysis: C$_{17}$H$_{24}$O$_5$NCl (M.W. 357.88)—Calculated: C, 57.04%; H, 6.77%; N, 3.91%; Cl, 9.90%. Found C, 57.29%; H, 7.02%; N, 3.66%; Cl, 9.65%.

EXAMPLE 5 p-isobutylphenyl acetyl carnitine hydrochloride 5.5 g (0.028 moles) of carnitine hydrochloride are dissolved in 9 mls of CF$_3$COOH, and to the solution an excess (20 mls) of p-isobutylphenyl acetyl chloride is added and the mixture is kept under stirring at 40°–45° C. for 4–5 hours. At the end of this period of time the mixture is partitioned with H$_2$O—CHCl$_3$, the organic phase is discarded and the aqueous phase is concentrated at reduced pressure at a bath temperature of about 50° C. A gelatinous raw material is obtained which is crystallized with isopropanol, the precipitate thus obtained is filtered, rapidly washed with ether because of its hygroscopicity, and dried under vacuum at a temperature not exceeding 50° C.; 6.8 g of a product are obtained (yield 65%) having the following characteristics:

M.P. 130°–32° C.

IR Spectrum (nujol) $\nu$co=1710 cm$^{-1}$ (acid); $\nu$co=1730 cm$^{-1}$ (ester).

NMR Spectrum (D$_2$O)$\delta$: 7.30 (m, 4H, arom.);

5.85 (m, H, —CH—);
          |
          O 3.82 (d, 2H, N$^+$—CH$_2$—);

3.21 (s, 9H, N$^+$(CH$_3$)$_3$);

2.91 (d, 2H, —CH$_2$COO); 2.46 (d, 2H, —CH$_2$—);

1.83 (m, H, —CH<); 0.92 (d, 6H, —(CH$_3$)$_2$);

Elementary analysis: C$_{19}$H$_{30}$ClNO$_4$ (M.W. 371.96)—Calculated: C, 61.35%; H, 8.06%; N, 3.76%; Cl, 9.53%. Found: C, 61.65%; H, 7.76%; N, 4.06%; Cl, 9.23%.

EXAMPLE 6 p-isobutylphenyl-α-methyl acetyl carnitine hydrochloride 4.95 g (0.025 moles) of D,L-carnitine hydrochloride are dissolved in 8 mls of CF$_3$COOH, and to the solution an excess (16 mls) of p-isobutylphenyl-alpha-methyl acetyl chloride is added and the mixture is kept under stirring at a temperature of 40°–45° C. for 4–5 hours. At the end of this period of time, the mixture is partitioned with H$_2$O—CHCl$_3$, the organic phase is discarded whereas the aqueous phase is concentrated under reduced pressure at a bath temperature of about 50° C. A gelatinous raw material is obtained which is crystallized with isopropanol. The precipitate thus obtained is filtered, rapidly washed with ether because of its hydroscopicity, and dried under vacuum at a temperature not exceeding 50° C.; 6.3 g of a product are obtained (yield 65%) having the following characteristics:

M.P. 190°–92° C.

IR Spectrum (nujol) $\nu$co=1710 cm$^{-1}$ (acid); $\nu$co=1735 cm$^{-1}$ (ester).

NMR Spectrum (D$_2$O)$\delta$: 7.22 (m, 4H, arom.);

5.77 (m, H, —CH—);
          |
          O 3.86 (d, 2H, N$^+$—CH$_2$—);

3.60 (m, H, OCOCH—); 3.30 (s, 9H, N$^+$(CH$_3$)$_3$);

2.90 (d, 2H, —CH$_2$COO); 2.40 (d, 2H, —CH$_2$—); 1.83 (m, 1H, —CH<);

1.50 (d, 3H, —C(CH$_3$)—); 0.85 (d, 6H, —(CH$_3$)$_2$);

Elementary analysis: C$_{20}$H$_{32}$O$_4$NCl (M.W. 385.99)—Calculated: C, 62.22%; H, 8.37%; N, 3.62%; Cl, 9.18%. Found: C, 62.77%; H, 7.87%; N, 3.42%; Cl, 9.38%.

EXAMPLE 7

Glutaryl carnitine hydrochloride 3.9 g (0.02 moles) of carnitine hydrochloride are dissolved in 6.5 mls (0.06 moles) of trifluoroacetic acid and subsequently caused to react with 3.0 g (0.02 moles) of glutarylchloride in a flask equipped with a dropping cooler with a CaCl$_2$-containing tube the flask being also provided of magnetic stirrer and kept in a bath whose temperature is maintained for the whole reaction period (12 hours) at a temperature of 40°–45° C.

The reaction mixture is treated with 60 cc of acetone under stirring and the little amount of solid which formed is filtered off. 130 cc of ethyl ether are slowly added under stirring till incipient precipitation by cooling in an ice-bath.

The somewhat deliquescent raw product which is collected by filtration (4.7 g) is once again crystallized and 4.02 g (71%) of solid product having the following characteristics are obtained:

NMR Spectrum (D$_2$O)$\delta$:

5.7 (m, 1H, C—H); 3.9 (d, 2H, N$^+$—CH$_2$);
         |
         O 3.2 (s, 9H, —N$^+$(CH$_3$)$_3$);

2.7 (m, 6H, —CH$_2$—CH$_2$—CH$_2$—);

IR Spectrum (nujol) $\nu$co=1740 cm$^{-1}$ (ester); $\nu$co=1730 cm$^{-1}$ (acid).

Elementary analysis: C$_{12}$H$_{21}$NO$_6$HCl M.W.=311.5—Calculated: C, 46.23%; H, 7.06%; N, 4.49%; Cl, 11.39%. Found: C, 45.98%; H, 7.05%; N, 4.40%; Cl, 11.22%.

EXAMPLE 8

Levulinyl carnitine hydrochloride 7.2 g (0.062 moles) of levulinic acid are esterified with 8 mls of conc. $H_2SO_4$ and 200 mls of absolute EtOH. The ethyl ester thus obtained (7.0 g; 0.048 moles) is treated with 8.2 mls of ethylene glycol and 0.112 g of p-toluensulfonic acid at 170° C. for 96 hours in anhydrous toluene. At the end of the reaction the organic phase is washed with a solution of saturated $NaHCO_3$ and $H_2O$, and subsequently dried on anhydrous $Na_2SO_4$. Upon drying the solution, 5 g (55%) of the ketal of the levulinic acid ethylester are obtained. The product thus obtained is dissolved in 40 mls of methanol and 40 mls of 1 N NaOH and kept at room temperature for 2 hours. 4 g of the ketal of the levulinic acid are obtained which are treated with 5 mls of $SOCl_2$ at 80° C. for 4 hours for preparing the acid chloride of the ketal of the levulinic acid. About 5 g of a slightly dark acid chloride are obtained which are added to 4.5 g (0.023 moles) of carnitine chloride dissolved in 10 mls of trifluoro acetic acid. The reaction mixture is kept under stirring at 50° C. overnight. Upon addition of 40 mls of acetone a thin precipitate forms which is filtered off. To the mixture 138 mls of cold (0° C.) ethyl ether are added and the mixture is allowed to stand under stirring overnight. From the solution 5.4 g of a raw white product separate which is further crystallized with ethyl ether. The product thus obtained (4.7 g) has the following characteristics:

NMR Spectrum $(D_2O)\delta$:

5.6 (m, 1H, CH); 3.9 (d, 2H, $N^+$—$CH_2$);
|
O

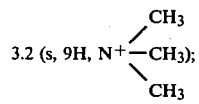

3.2 (s, 9H, $N^+$—$CH_3$);

2.9 (d, 2H, $CH_2CO$); 2.7 (m, 4H, —$CH_2$—$CH_2$); 2.2 (s, 3H, $COCH_3$)

IR Spectrum (nujol) $\nu_{CO}=1755$ cm$^{-1}$ (C=O ester); $\nu_{CO}=1710$ cm$^{-1}$ (C=O acid).

Elementary analysis: $C_{12}H_{21}O_5N.HCl$ (M.W. 295.5)—Calculated: C, 48.73%; H, 7.44%; N, 4.73%; Cl, 12.01%. Found: C, 49.01%; H, 7.41%; N, 4.90%; Cl, 12.35%.

EXAMPLE 9

β-ketoglutaryl carnitine hydrochloride 6.4 g (0.043 moles) of β-ketoglutaric acid are treated at 80° C. for 4 hours with 6 mls of conc. $H_2SO_4$ and 200 mls of absolute ethyl alcohol. The ethyl ester which forms (6.5 g; 0.037 moles) is reacted with 9 mls of ethylene glycol and 0.120 mg of para-toluensulfonic acid under reflux conditions for 72 hours in anhydrous toluene.

The reaction mixture is washed with a saturated solution of $NaHCO_3$, with water and after drying on anhydrous $Na_2SO_4$ concentrated to dryness under vacuum. Upon drying the solution, 4.8 g (65%) of the ketal of the β-ketoglutaric acid ethylester are obtained. The solid thus obtained is dissolved in 45 mls of methyl alcohol and 40 mls of 1 N NaOH and kept at room temperature for 2 hours under stirring.

3.8 g (0.02 moles) (90%) of the ketal of the β-ketoglutaric acid are obtained which are treated with 6 mls of thionyl chloride at 80° C. for 6 hours in order to prepare the corresponding acid chloride. The acid chloride thus obtained is added slowly to 4.2 g (0.022 moles) of carnitine hydrochloride dissolved in trifluoroacetic acid, the mixture is kept under stirring for 12 hours at 60° C., then cooled to 0° C. 40 cc of acetone are added thereto. A slight cloud forms which is eliminated by centrifugation. To the centrifugated solution, 130 mls of ethyl ether at 0° C. are added. A white precipitate forms which is once again crystallized with ethyl ether. 6.3 g of a product having the following characteristics are obtained:

NMR Spectrum $(D_2O)\delta$:

5.8 (m, 1H, CH); 3.8 (d, 2H, $N^+$—$CH_2$);
|
O

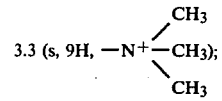

3.3 (s, 9H, —$N^+$—$CH_3$);

2.9 (d, 2H, $CH_2$—CO); 2.7 (s, 4H, $CH_2$—CO—$CH_2$—)

IR Spectrum (nujol) $\nu_{CO}=1740$ cm$^{-1}$ (ester); $\nu_{CO}=1718$ cm$^{-1}$ (acid).

Elementary analysis: $C_{12}H_{20}O_7N.HCl$ (M.W. 326.5)—Calculated: C, 44.10%; H, 6.43%; N, 4.28%; Cl, 10.87%. Found: C, 44.06%; H, 6.29%; N, 4.20%; Cl, 10.60%.

EXAMPLE 10

Fumaryl carnitine hydrochloride

To 4.5 (0.023 moles) of carnitine hydrochloride dissolved in 10 mls of trifluoroacetic acid and heated to 40° C., 3.09 g (0.023 moles) of the chloride of the fumaric acid are slowly added under vigorous stirring. The reaction mixture is kept under stirring for 12 hours taking care that the temperature does not exceed 40° C. and shielding the reaction flask with a $CaCl_2$-containing tube.

The mixture is then cooled to 0° C. with an ice-bath and slowly 60 cc of acetone are added. The solution becomes cloudy and is then centrifugated. To the clear solution, 120 cc of a mixture ethyl ether:hexane (1:1) is slowly added. A raw product (5.4 g) is obtained as an oil which slowly solidifies. Upon crystallizaton with further mixture ether-hexane (1:1), 4.65 g of a product having the following characteristics, are obtained:

NMR Spectrum $(D_2O)\delta$:

6.7 (s, 2H, —CH=CH—); 5.8 (m, 1H, CH);
|
O

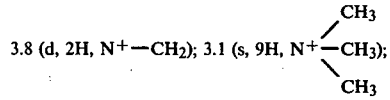

3.8 (d, 2H, $N^+$—$CH_2$); 3.1 (s, 9H, $N^+$—$CH_3$);

2.6 (d, 2H, $CH_2$—CO)

IR Spectrum (nujol) $\nu_{CO}=1730$ cm$^{-1}$ (ester); $\nu_{CO}=1725$ cm$^{-1}$ (acid).

Elementary analysis: $C_{11}H_{18}O_6N \cdot HCl$ (M.W. 295.7)—Calculated: C, 44.64%; H, 6.42%; N, 4.73%; Cl, 12.00%. Found: C, 44.38%; H, 6.59%; N, 4.91%; Cl, 11.83%.

EXAMPLE 11

N-acetyl glutamyl carnitine hydrochloride 4.2 g (0.021 moles) of carnitine hydrochloride are dissolved in 12 mls of trifluoroacetic acid, then at 35° C. and under vigorous stirring 20 cc of a solution of anhydrous chloroform wherein about 4.36 g (0.021 moles) of the acide chloride of the N-acetyl glutamic acid have been dissolved are added dropwise. The reaction is allowed to proceed for about 14 hours at 35° C., and subsequently at 50° C. for two further hours. The reaction mixture is cooled. Upon acetone addition (40 mls) no precipitate forms even though the mixture is cooled below 0° C. 140 mls of ethyl ether are added and after keeping the mixture at 8° C. overnight there are obtained 6.2 g of a solid white product which is crystallized with ethyl ether. After 2 crystallizations 5.4 g (68%) of the desired product having the following characteristics are obtained:

NMR Spectrum ($D_2O$)δ:

5.6 (m, 1H, CH); 3.8 (d, 2H, $N^+$—CH$_2$);
|
O

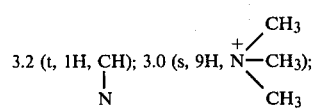

2.6 (d, 2H, CH$_2$CO); 2.0 (m, 7H, CH$_2$—CH$_2$, CO—CH$_3$)

IR Spectrum (nujol) $\nu co = 1745$ cm$^{-1}$ (ester); $\nu co = 1725$ cm$^{-1}$ (acid).

Elementary analysis: $C_{14}H_{24}N_2O_7 \cdot HCl$ (M.W.=367.3)—Calculated: C, 45.74%; H, 6.53%; N, 7.62%; Cl, 9.66%. Found: C, 45.60%;, H, 6.41%; N, 7.90%; Cl, 9.99%.

EXAMPLE 12

N,S-diacetylcysteinyl carnitine acid chloride

To a solution of carnitine hydrochloride (1.58 g; 0.008 moles) in trifluoroacetic acid (5 ml) the acid chloride of N, S diacetyl cysteine (1.78 g; 0.008 moles) in trifluoro acetic acid (8 ml) is added. The mixture is kept at room temperature overnight. Acetone (50 mls) is added and the mixture is allowed to stand under cold conditions for 4 hours, the precipitated carnitine is filtered off and to the solution ethyl ether (50 mls) is added. The mixture is further kept under stirring at room temperature for 1 hour; a pitchy solid precipitates which is separated by decantation and crystallized from isopropanol-acetone. 1.54 g (yield 50%) are obtained:

M.P. 154°–158° C.

NMR Spectrum ($D_2O$)δ:

8.2 (d, 2H, CONH); 5.5 (m, 1H, CH);
|
O

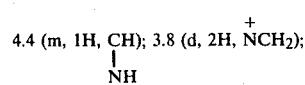

4.4 (m, 1H, CH); 3.8 (d, 2H, $\overset{+}{N}CH_2$);
|
NH 3.1 (s, 9H, $N^+$(CH$_3$)$_3$); 2.85 (d, 2H, CH$_2$S);

2.6 (d, CH$_2$CO); 1.9 (s, 6H, S—COCH$_3$ / N—COCH$_3$)

IR Spectrum (nujol) $\nu co = 1750$ cm$^{-1}$ (ester); $\nu co = 1710$ cm$^{-1}$ (acid).

Elementary analysis: $C_{14}H_{25}N_2O_6SCl$— Calculated: C, 43.68%; H, 6.55%; N, 7.28%. Found: C, 43.13%; H, 6.80%; N, 7.15%.

EXAMPLE 13

N-acetylvalyl carnitine acid chloride

To 2.8 g (0.014 moles) of carnitine hydrochloride dissolved in 8 mls of trifluoroacetic acid, 2.48 g (0.014 moles) of acetylvaline acid chloride are slowly added under constant stirring. Acetylvaline acid chloride was previously prepared by reacting acetylvaline with an excess of thionyl chloride. The mixture is allowed to react overnight under vigorous stirring in a thermostatic bath at 40° C. by carefully excluding moisture presence with a CaCl$_2$-containing tube. The thin precipitate which is obtained upon addition of 40 mls of acetone is filtered off. To the residual mixture 120 mls of ethyl ether are then added. After 4 hours at 0° C. 3.46 g of a raw, hygroscopic, solid product which upon further crystallization becomes 3.12 g (63%) are obtained. This product has the following characteristics:

NMR Spectrum ($D_2O$)δ:

5.6 (m, 1H, CH); 4.0 (d, 1H, CH);
|           |
O           NH

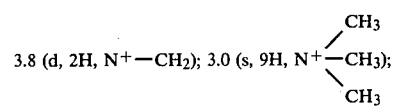

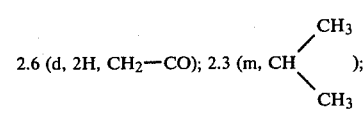

2.0 (s, 3H, COCH$_3$); 1.1 (s, 3H, CH$_3$); 1.0 (s, 3H, CH$_3$)

IR Spectrum (nujol) $\nu co = 1740$ cm$^{-1}$ (ester); $\nu co = 1718$ cm$^{-1}$ (acid).

Elementary analysis; $C_{14}H_{27}N_2O_6 \cdot HCl$ (M.W.=354.85)— Calculated: C, 47.21%; H, 7.87%; N, 6.74%; Cl, 9.97%. Found: C, 46.92%; H, 7.635; N, 6.71%; Cl, 9.83%.

EXAMPLE 14

Pyruvyl carnitine hydrochloride

The title compound is prepared according to the following two processes:

Process (a): According to this process, there is first obtained the acid chloride of the pyruvic acid (CH$_3$COCOCl) which is then reacted with carnitine hydrochloride.

To a mixture of anhydrous sodium carbonate (10.6 g; 0.1 moles), anhydrous dimethylformamide (0.1 ml) and pyruvic acid (13.9 mls; 0.2 moles) in anhydrous ethyl ether (125 mls) kept at 0° C., oxalyl chloride diluted in 25 mls of anhydrous ether in an amount equimolar to the pyruvic acid (17.1 mls; 0.2 moles) is added dropwise. The resulting mixture is allowed to stand under stirring for 24 hours. The reaction mixture is then filtered and the filtrate is distilled, collecting the fraction distilling at 53° C./126 torr. Yield: 20%.

Alternatively, the pyruvic acid chloride is also prepared by adding dropwise under stirring at room temperature to pyruvic acid (7 mls; about 0.1 moles) methyl-dichloro methyl ether (9 mls; about 0.1 moles). At the end of the addition, the reaction mixture is heated up to 50° C. and kept at this temperature for 30 minutes. The mixture is then distilled, collecting the fraction distilling at 53° C./126 torr.

The pyruvyl chloride obtained with either one of the foregoing methods is added to a solution of carnitine hydrochloride (10 g) dissolved in trifluoroacetic acid (25 mls). The resulting mixture is allowed to stand at 40° C. overnight. The mixture is then cooled with ice and 40 mls of acetone are added thereto. After 2 hours, the precipitate is filtered off.

To the filtrate 100 mls of ethylether are added dropwise thus obtaining an oil. This oil is purified by dissolving it with a mixture 5:1 EtOH/acetone and adding ethyl ether which causes the formatiodn of a precipitate, which upon analysis turns out to be the title compound.

$C_{10}H_{18}ClNO_5$: M.W. 267.71— Elementary Analysis: C=44.87%; H=6.78%; N=5.23%; Cl=13.24%.

NMR spectrum: ($D_2O$) 5.6 (m, 1H, $CH_2$—CH—$CH_2$)) 3.8 (d, 2H, mH—$CH_2$); 3.3. (s, 9H, N ($CH_3$)$_3$); 2.8 (d, 2H, —$CH_2$—CO—); 2.1 (s, 3H, $CH_3$).

Process (b): According to this process, there is first obtained the mixed anhydride of the pyruvic acid which is then reacted with carnitine perchlorate, thus obtaining the title compound (isolated as pyruvyl carnitine perchlorate). Pyruvic acid (8.8 g; 0.1 moles) is dissolved in 100 mls of acetonitrile and equimolar amounts (with respect to the pyruvic acid) of triethylamine (10.1 g; 0.1 moles) and ethyl- or isobutylchloroformate (0.1 moles) are added at a temperature between −10° C. and 0° C.

The resulting reaction mixture is kept at 0° C. for 1 hour; the triethylamine hydrochloride is filtered off and the filtrate containing the mixed anhydride is added to a solution of carnitine perchlorate prepared as follows: carnitine hydrochloride (10 g) is suspended in $CH_3CN$ (150 mls) and silver perchlorate (12 g) is added thereto. The mixture is allowed to stand in the dark under stirring for about 30 minutes and then the precipitated silver chloride is filtered off.

The reaction mixture is kept at 40° C. overnight. The mixture is then cooled and filtered. To the filtrate ethyl ether is added thus obtaining an oil which is purified by dissolving it in EtOH/acetone 5:1 dl and by further precipitation with ether. The following compound is obtained:

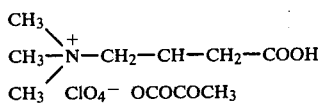

Elementary Analysis C=36.12% H=5.47% Cl=10.69% N=4.22%.

NMR: identical to that of the compound obtained by process (a).

Therapeutic Applications of the Acyl-carnitine derivatives of formula (I)

The tolerance of the Acyl-carnitines of the formula (I), as well as their salts administered by intraperitoneal route was investigated in mice using the Weil Method (1). As indicated by the $LD_{50}$ values given in Table 1 below, all the acyl derivatives of carnitine exhibit good tolerance.

The cardiokinetic effect on isolated heart was also investigated as follows. Rabbit hearts isolated by the Langendorff method were perfused with oxygenized ringer solution at 38.2° C. The isometric contractions, electrocardiogram and coronary flow were recorded using a "Battaglia-Rangoni" polygraph. By removing the oxygen from the perfusion fluid, metabolic damage was induced in the cardiac muscle, up to an 80% reduction in the cardiac contractile force.

Under these conditions of prolonged anoxia the aerobic glycolysis of the myocardium is slowed down, accompanied by the storage of acid catabolites due to both the accumulation of pyruvic acid and its conversion to lactic acid which cannot be utilized because of the depression of pyridine enzymes, such as LDH (lactodehydrogenase). This has repercussions on the anaerobic glycolysis affecting an ever increasing number of enzymes, accompanied by a progressive and increasingly critical exhaustion of the myocardium. Thus a whole series of cardiac muscle fatigue levels occurs which can be observed by the behavior of the examined parameters, namely the contractile force, coronary flow, heart rate and cardiac rhythm. As soon as the contractile force was reduced by 80%, the perfusion fluid was once again oxygenized either without adding other compounds (controls) or with the addition of the compounds under examination.

Table 2 below gives the percentage values of the contractile force of the heart, showing a positive inotropic effect, calculated after 10 minutes from the interruption of the anoxic period (myocardial restoration).

The results, evaluated by means of Student's "t" test, show that at equal concentrations in the perfusion fluid, trifluoromethyl cinnamoyl, cinnamoyl, pivaloyl, bromopropionyl, dipropyl acetyl and piruvyl induce a greater positive inotropic effect than that of the other compounds under examination, with statistically significant differences as compared with the controls.

The coronary vasodilator effect was also investigated with the results described herein below. All the compounds of formula (I) under examination provoke, as compared with controls, a small statistically non-significant increase in coronary flow.

The chronotropic effect was examined, and all the compounds of the formula (I) under examination did not significantly change heart rate versus controls.

The antiarrhythmic effect was also investigated and it was found that by using the isolated rat ventricle method described by M. Libonati and G. Segre (2) among the compounds of the formula (I) under examination, pyruvyl, trifluoromethyl cinnamoyl, pivolyl, chlorobutyryl, dipropilacetyl are especially useful since they possess the most clear out antiarrhythmic properties. These results are shown in Table 3 hereinbelow.

The antiarrhythmic effect of the compounds was also investigated in mice according to the P. W. Nwangwu, T. Holcslow procedure (4). Using Aconitine (5 mg/ml) as arrhythmogenic agent, the changes in the cardiac rhythm of the animals were recorded and the onset time of initial arrhythmia and/or of ventricular tachycardia were used as End point.

Antiarrhythmic agents display an increase in the latency time of initial ECG change.

The results reported in Table IV show that the compounds are endowed with antiarrhythmic activity which is markedly exhibited by dipropyl-acetyl, cyclohexyl propionyl, trifluoromethyl cinnamoyl, methoxycinnamoyl and pyruvyl.

The antagonism to adrenaline-induced toxicity was also investigated with the following results. Groups of ten male albino Swiss mice were injected with adrenaline (tartrate) intraperitoneally at progressive logarithmic doses. Other similar groups of animals were injected with 150 mg/kg of the compounds under examination via the same route, 30 minutes before adrenaline administration. Mortality was assessed by means of the Litchfield and Wilcoxon method (3) 36 hours after adrenaline administration.

These results are shown in Table V hereinbelow.

Therefore, of all the previously mentioned compounds and their pharmaceutically acceptable salts are the most preferred in the therapy of heart diseases of the anoxic, ischaemic, arrhythmic and cardiotoxic types, as well as in those cases where the energy requirement of the heart increases.

The antilipoemic effect of some acyl-derivatives of the formula (I) have been studied under two different experimental conditions.

In 17-hrs fasted rats the F.F.A. (fatty-free acids) splasms levels were reduced by a single i.p. administration with 500 mg kg$^{-s}$ of d,l dipropyl ACAR; l dipropyl ACAR (ACAR=acetylcarnitine); d,l exanoyl CAR (CAR=carnitine) and d,l pyruvyl CAR.

The decrease, compared with untreated animals, was $-35\%$, $-29\%$, $-41\%$ and $-65\%$ respectively.

In the rats the lipoproteic pattern altered due to an oil administration by gavage, was restored after a single treatment with d,l dipropyl ACAR; d,l ethyl exanoyl CAR; d,l 3 bromopropionyl CAR and d,l pyruvyl CAR. The most marked effect, displayed by the increase of the HDL (high density lipoprotein fraction) and the decrease of the LDL and VLDL (low density lipoprotein and very low density lipoprotein fractions) was exhibited by the d,l pyruvyl derivative which was shown to be active against the triglycerides and cholesterol plasma levels which increased after oil assumption.

The results are reported in Table VI.

PHARMACEUTICAL PREPARATIONS

1. Solutions and sterile aqueous solutions containing acyl-carnitines in concentrations from 25 mg to 500 mg per ml.

(a) The excipient for injectable ampoules/vials is prepared in accordance with the following non-limitative composition:

| | |
|---|---|
| sodium carboxymethyl cellulose (at low viscosity) | 10 mg/ml |
| polysorbate 80 | .4 mg/ml |
| propylparaben | 0.4 mg/ml |
| water for injections sufficient for 1 ml, 2 ml, 5 ml and 10 ml ampoules/vials | |

(b) The excipient for phlebocylsis bottles containing 50 ml, 100 ml, 250 ml, 500 ml and 1000 ml is prepared in accordance with the following non-limitative composition:

| | |
|---|---|
| NaCl | 8.6 g/lt |
| KCl | .3 g/lt |
| CaCl$_2$ | .33 g/lt |
| water for injections sufficient for 1 liter. | |

(c) The excipient for bottles for oral use containing from 5 ml to 100 ml is prepared in accordance with the following non-limitative composition;

| | |
|---|---|
| mannitol | 11 mg/ml |
| sorbitol | 600 mg/ml |
| sodium benzoate | 3 mg/ml |
| orange extract | 200 mg/ml |
| vitamin B$_{12}$ | 3 mcg/ml |
| sufficient purified water | |

2. Tablets containing from 20 mg to 500 mg of acyl-carnitine or any one of the derivatives under examination. The excipient is prepared in accordance with the following non-limitative composition:

| | |
|---|---|
| starch | 45% |
| avicol | 45% |
| talc | 10% |

3. Capsules containing from 20 mg to 500 mg of acyl-carnitine or any one of the derivatives under examination, without excipients in a non-limitative sense.

4. Aerosol and spray preparations from 50 mg to 10 g acyl-carnitine or any one of the derivatives under examination. The excipient is prepared in accordance with the following non-limitative composition:

| | |
|---|---|
| ethanol | 30% |
| purified water | 30% |
| sufficient freon 12/114 (50 parts/50 parts). | |

TEST METHODS (1) Weil C. S., Biometr. J. 8, 249, 1952

(2) M. Libonati and G. Segre, Archivio Italiano di Scienze Farmacologiche. Serie XIII, Vol. X, pag. 3, (1960)

(3) Litchfield S. I., Wilcoxon F., J. Pharmacolog. Exp. Ther. 96, 99, (1949)

(4) P. W. Nvangvu, T. L. Holcslow, Arch. Int. Pharmacodyn. 229, 219 (1977)

TABLE I

LD$_{50}$, mg kg$^{-1}$ i.p. in mice, of some acyl derivatives of formula (1). Weil method (N = 5, K = 4)

| Derivatives | | LD$_{50}$ and fiducial limits mg kg$^{-1}$ i.p. |
|---|---|---|
| d,l diethyl | ACAR | 1200 (900–1500) |
| d,l dipropyl | ACAR | 1700 (1450–1950) |
| l dipropyl | ACAR | 294 (242–357) |
| d dipropyl | ACAR | 1600 (1840–1360) |

TABLE I-continued

LD$_{50}$, mg kg$^{-1}$ i.p. in mice,
of some acyl derivatives of formula (1).
Weil method (N = 5, K = 4)

| Derivatives | | LD$_{50}$ and fiducial limits mg kg$^{-1}$ i.p. |
|---|---|---|
| d,l 3-Br—propionyl | CAR | 950 (780–1120) |
| l 3-Br—propionyl | " | 960 (775–1125) |
| d,l 4-Cl—butyryl | " | 850 (690–1010) |
| d,l pivaloyl | " | 855 (745–965) |
| l pivaloyl | " | 618 (232–720) |
| d,l cyclohexyl | " | 850 (690–1010) |
| d,l cyclohexylpropionyl | " | 955 (775–1125) |
| d,l 2-ethylhexanoyl | " | 950 (770–1120) |
| d,l cinnamoyl | " | 1120 (980–1260) |
| d,l p-methylcinnamoyl | " | 620 (550–690) |
| d,l trifluoromethylcinnamoyl | " | 845 (785–910) |
| l trifluoromethylcinnamoyl | " | 540 (500–580) |
| d,l p-chlorocinnamoyl | " | 935 (870–995) |
| d,l p-methoxycinnamoyl | " | 440 (400–480) |
| d,l m-bromocinnamoyl | " | 650 (590–710) |
| d,l naphtalene | ACAR | 880 (750–1010) |
| d,l p-isobutyl phenyl | ACAR | 378 (293–489) |
| d,l pyruvyl | CAR | 3900 (3250–4450) |

TABLE II

The effect
of some acyl derivatives of formula (I) on the contractile
force of rabbit's heart. (Details are given in the text)

| Derivatives | | Concentration g l$^{-1}$ | Contractile force mean ± SEM | P |
|---|---|---|---|---|
| Krebs solution (control) | | | 27.45 ± 5.28 | |
| d,l diethyl | ACAR | 1·10$^{-5}$ | 49.25 | ≦0.05 |
| d,l dipropyl | ACAR | " | 70.12 | ≦0.01 |
| l dipropyl | ACAR | " | 55.46 | ≦0.05 |
| d dipropyl | ACAR | " | 45.34 | ≦0.05 |
| d,l 3-Br—propionyl | CAR | " | 65.64 | ≦0.01 |
| l 3-Br—propionyl | " | " | 70.26 | ≦0.01 |
| d,l 4-Cl—butyryl | " | " | 40.12 | n.s. |
| d,l pivaloyl | " | " | 65.15 | <0.05 |
| l pivaloyl | " | " | 68.26 | <0.01 |
| d,l cyclohexyl | " | " | 40.42 | n.s. |
| d,l cyclohexylpropionyl | " | " | 54.23 | n.s. |
| d,l 2-ethylhexanoyl | " | " | 23.12 | n.s. |
| d,l cinnamoyl | " | " | 60.65 | ≦0.01 |
| d,l p-methylcinnamoyl | " | " | 44.16 | n.s. |
| d,l trifluoromethylcinnamoyl | " | " | 84.26 | ≦0.001 |
| l trifluoromethylcinnamoyl | " | " | 51.12 | ≦0.01 |
| d,l p-chlorocinnamoyl | " | " | 46.14 | ≦0.05 |
| d,l p-methoxycinnamoyl | " | " | 40.26 | n.s. |
| d,l m-bromocinnamoyl | " | " | 50.14 | n.s. |
| d,l naphtalene | ACAR | " | 63.48 | ≦0.01 |
| d,l p-isobutyl phenyl | ACAR | " | 57.57 | ≦0.05 |
| d,l pyruvyl | CAR | " | 88.61 | ≦0.001 |

TABLE III

The antiarrhythmic
effect of some acyl derivatives (concentration 1·10$^{-6}$ M.)
of the formula (1) on the rat's ventricle strip test.
% variation versus basal value.

| Derivatives | | maximed frequency (− %) | refractory period (+ %) | whole excitability (− %) | rheobase (+ %) |
|---|---|---|---|---|---|
| Quinidine | | 72.45 | 57.43 | 191.15 | 51.23 |
| d,l diethyl | ACAR | 25.15 | 31.17 | 27.48 | 20.61 |
| d,l dipropyl | ACAR | 23.18 | 34.26 | 50.65 | 24.19 |
| l dipropyl | ACAR | 25.29 | 39.12 | 58.25 | 55.12 |
| d propyl | ACAR | 22.45 | 38.26 | 25.48 | 21.71 |
| d,l 3-Br—propionyl | CAR | 17.29 | 40.25 | 39.68 | 26.15 |
| l 3-Br—propionyl | " | 50.45 | 45.12 | 60.25 | 42.38 |
| d,l 4-Cl—butyryl | " | 60.25 | 38.26 | 55.12 | 35.24 |
| d,l pivaloyl | " | 58.36 | 40.65 | 65.48 | 40.25 |
| l pivaloyl | " | 60.41 | 38.27 | 48.12 | 35.14 |
| d,l cyclohexyl | " | 22.12 | 15.78 | 26.45 | 18.23 |
| d,l cyclohexylpropionyl | " | 45.26 | 12.48 | 25.46 | 22.45 |
| d,l 2-ethylhexanoyl | " | 25.50 | 22.84 | 40.26 | 21.78 |
| d,l cinnamoyl | " | 29.75 | 40.12 | 75.28 | 49.56 |
| d,l p-methylcinnamoyl | " | 38.64 | 45.26 | 71.12 | 32.44 |
| d,l trifluoromethylcinnamoyl | " | 41.26 | 25.74 | 24.32 | 19.47 |
| l trifluoromethylcinnamoyl | " | 32.71 | 40.12 | 60.48 | 39.19 |
| d,l p-chlorocinnamoyl | " | 25.12 | 22.34 | 22.17 | 20.45 |
| d,l p-methoxycinnamoyl | " | 22.17 | 36.14 | 31.46 | 22.24 |
| d,l m-bromocinnamoyl | " | 28.51 | 45.16 | 50.43 | 38.12 |
| d,l naphtalene | ACAR | 41.17 | 39.28 | 40.15 | 41.18 |
| d,l p-isobutyl phenyl | ACAR | 38.25 | 22.47 | 35.16 | 22.18 |
| d,l pyruvyl | CAR | 80.15 | 50.17 | 95.46 | 48.18 |

TABLE IV

Effect of some acyl derivatives of formula (1)
on the arrhythmia induced by Aconitine (5 γ/ml) in mice.
% increase of the time to onset of initial cardiac arrythmia
confered to control group.

| Derivatives | | Concentration mg kg$^{-1}$ i.v. | latency time increase % of controls | |
|---|---|---|---|---|
| | | | arrhythmias | tachycardia |
| Quinidine | | 89 | 50 | 41.7 |
| d,l diethyl | ACAR | 300 | 25 | 32 |
| d,l dipropyl | ACAR | 150 | 65 | 55 |
| l dipropyl | ACAR | 40 | 60 | 40 |
| d dipropyl | ACAR | 40 | 50 | 30 |
| d,l 3-Br—propionyl | CAR | 150 | 20 | 10 |
| l 3-Br—propionyl | " | 150 | 25 | 12 |
| d,l 4-Cl—butyryl | " | 300 | 20 | 10 |
| d,l pivaloyl | " | 300 | 20 | 10 |
| l pivaloyl | " | 300 | 25 | 15 |
| d,l cyclohexyl | " | 300 | 50 | 38 |
| d,l cyclohexylpropionyl | " | 150 | 70 | 55 |
| d,l 2-ethylhexanoyl | " | 300 | 20 | 10 |
| d,l cinnamoyl | " | 150 | 20 | 8 |
| d,l p-methylcinnamoyl | " | 150 | 20 | 9 |
| d,l trifluoromethylcinnamoyl | " | 40 | 50 | 30 |
| l trifluoromethylcinnamoyl | " | 40 | 60 | 45 |
| d,l p-chlorocinnamoyl | " | 300 | 25 | 10 |
| d,l p-methoxycinnamoyl | " | 150 | 70 | 56 |
| d,l m-bromocinnamoyl | " | 150 | 40 | 28 |
| d,l naphtalene | ACAR | 75 | 25 | 10 |
| d,l p-isobutyl phenyl | ACAR | 300 | 20 | 10 |
| d,l pyruvyl | CAR | 40 | 80 | 60 |

TABLE V

The effect of some acyl derivatives of formula (1) on the cardiotoxic effect induced by Adrenaline in mice.

| Derivatives | | | LD$_{50}$ and fiducial limits mg dg$^{-1}$ e.v. |
|---|---|---|---|
| Saline | | + Adrenaline | 5.50 (4.35–6.15) |
| d,l diethyl | ACAR | " | 10.26 (8.12–12.40) |
| d,l dipropyl | ACAR | " | 12.58 (9.47–15.69) |
| l dipropyl | ACAR | " | 11.25 (8.45–14.00) |
| d dipropyl | ACAR | " | 9.48 (6.12–12.84) |
| d,l 3-Br—propionyl | CAR | | 10.12 (8.45–11.89) |
| l 3-Br—propionyl | " | | 15.27 (11.12–19.42) |
| d,l 4-Cl—butyryl | " | | 14.83 (12.58–17.08) |
| d,l pivaloyl | " | | 5.48 (4.35–6.61) |
| l pivaloyl | " | | 5.25 (4.14–6.36) |
| d,l cyclohexyl | " | | 10.24 (8.12–12.36) |
| d,l cyclohexyl-propionyl | " | | 11.23 (9.05–13.41) |
| d,l 2-ethylhexanoyl | " | | 7.14 (4.89–9.39) |
| d,l cinnamoyl | " | | 6.34 (5.02–7.66) |
| d,l p-methylcinnamoyl | " | | 6.88 (5.24–8.52) |
| d,l trifluoromethyl-cinnamoyl | " | | 7.12 (5.98–8.26) |
| l trifluoromethyl-cinnamoyl | " | | 7.28 (5.44–9.12) |
| d,l p-chlorocinnamoyl | " | | 10.15 (8.32–12.08) |
| d,l p-methoxy-cinnamoyl | " | | 6.84 (5.12–8.56) |
| d,l m-bromocinnamoyl | " | | 7.18 (5.28–9.08) |
| d,l naphtalene | ACAR | | 7.43 (5.14–9.72) |
| d,l p-isobutyl phenyl | ACAR | | 8.75 (6.45–11.05) |
| d,l pyruvyl | CAR | | 14.07 (11.12–17.02) |

TABLE VI

The effect of some acyl derivatives of formula (I) on plasma cholesterol, triglycerides and lipoproteins in rat treated with olive oil, 15 ml kg$^{-1}$ orally. Mean Values ± SEM

| | Derivatives mg Kg$^{-1}$ ip | | | triglycerides mg/100 ml | cholesterol mg/100 ml | Lipoproteins % | | |
|---|---|---|---|---|---|---|---|---|
| | | | | | | HDL | VLDL | LDL |
| normal animals | none | | | 78.16 ± 6.40 ▲ | 68.22 ± 3.20 ▲ | 35.79 ± 2.63 | 10.23 ± 1.19 Δ | 49.12 ± 2.71 Δ |
| control group | none | | oil | 213.66 ± 28.68 | 88.33 ± 2.96 | 24.18 ± 2.15 | 15.84 ± 1.53 | 57.38 ± 2.25 |
| | d,l dipropyl ACAR | | " | 121.50 ± 11.13 □ | 75.15 ± 3.11 □ | 28.13 ± 3.27 ns | 13.26 ± 2.03 ns | 50.12 ± 2.08 Δ |
| treated animals | d,l diethyl exanoyl | CAR | " | 178.15 ± 12.45 ns | 79.10 ± 3.84 ns | 28.37 ± 2.98 ns | 13.88 ± 1.63 ns | 52.14 ± 2.95 ns |
| | d,l 3-Br—propionyl | CAR | " | 123.48 ± 12.16 □ | 76.18 ± 3.02 □ | 30.45 ± 2.87 □ | 11.22 ± 1.22 ns | 51.26 ± 2.49 Δ |
| | d,l pyruvyl | CAR | " | 85.14 ± 7.22 ▲ | 70.26 ± 2.74 ▲ | 33.26 ± 2.17 ▲ | 10.15 ± 1.03 ▲ | 50.15 ± 2.33 ▲ |

Student "t" test □, Δ and ▲ indicate respectively a non significant difference, a P ≦ 1% and 1%.
N = 8

What is claimed is:

1. Acyl derivatives of carnitine having the general formula:

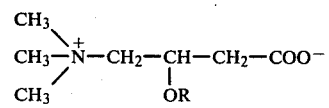

wherein R is the monovalent radical of the following organic acids: 3-bromopropionic, 4-chorobutyric, cyclohexylcarboxylic, cyclohexylpropionic, α-methylenebutyric, β-methylenebutyric, cinnamic, p-methylcinnamic, p-chlorocinnamic, p-methoxycinnamic, m-trifluoromethylcinnamic, m-bromocinnamic, phenylacetic, p-isobutylphenylacetic, p-methylphenylacetic, p-ethylphenylacetic, p-cyclohexylphenylacetic, p-cyclopropylphenylacetic, p-isobutyl m-chlorophenylacetic, α-phenylpropionic, p-isobutyl, α-phenylpropionic, p-methyl, α-phenylpropionic, p-ethyl α-phenylpropionic, p-cyclohexyl α-phenylpropionic, p-cyclopropyl α-phenylpropionic, p-isobutyl α-phenylpropionic, 2-naphthalene acetic, malonic (monoester), glutaric (monoester), α-methylglutaric (monoester), adipic (monoester), pimelic (monoester), suberic (monoester), azelaic (monoester), sebacic (monoester), α-methyl-α-hydroxy glutaric (monoester), fumaric (monoester), citric (monoester), isocitric (monoester), pyruvic, levulinic, α-ketoglutaric (monoester), β-ketoglutaric (monoester), oxalacetic, γN-acetylaminobutric, εN-acetylaminocaproic, N-acetylaspartic (monoester), N-acetylglutamic (monoester), N-acetyl-5 aminoglutamic (monoester), N-acetylcysteine, S, N-diacetylcysteine, N-acetyl leucine, N-acetyl isolelucine, N-acetylmethionine, and N-acetylvaline.

2. The acyl-derivatives of carnitine of claim 1 in their optically active forms.

3. The acyl-derivatives of carnitine of claim 1 in their racemic form.

4. A pharmaceutically acceptable salt of the acyl-derivatives of claim 1.

5. A pharmaceutical composition for the treatment of cardiac disorders, hyperlipoproteinaemias and hyperlipemias comprising an effective amount of an acyl-derivative of carnitine of claim 1.

* * * * *